(12) United States Patent
Davies

(10) Patent No.: US 11,963,823 B2
(45) Date of Patent: Apr. 23, 2024

(54) RADIOPAQUE ARRANGEMENT OF ELECTRONIC COMPONENTS IN INTRA-CARDIAC ECHOCARDIOGRAPHY (ICE) CATHETER

(71) Applicant: KONINKLIJKE PHILIPS N.V., Eindhoven (NL)

(72) Inventor: Stephen Charles Davies, El Dorado Hills, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 762 days.

(21) Appl. No.: 16/338,838

(22) PCT Filed: Sep. 26, 2017

(86) PCT No.: PCT/IB2017/055829
§ 371 (c)(1),
(2) Date: Apr. 2, 2019

(87) PCT Pub. No.: WO2018/065849
PCT Pub. Date: Apr. 12, 2018

(65) Prior Publication Data
US 2019/0247018 A1 Aug. 15, 2019

Related U.S. Application Data

(60) Provisional application No. 62/512,880, filed on May 31, 2017, provisional application No. 62/403,245, filed on Oct. 3, 2016.

(51) Int. Cl.
*A61B 8/00* (2006.01)
*A61B 6/00* (2006.01)
(Continued)

(52) U.S. Cl.
CPC .............. *A61B 8/4245* (2013.01); *A61B 6/12* (2013.01); *A61B 6/463* (2013.01); *A61B 6/5247* (2013.01);
(Continued)

(58) Field of Classification Search
None
See application file for complete search history.

(56) References Cited

U.S. PATENT DOCUMENTS

| 5,947,905 A | 9/1999 | Hadjicostis et al. | |
| 2004/0193057 A1* | 9/2004 | Barbato | A61B 8/4461 600/459 |

(Continued)

FOREIGN PATENT DOCUMENTS

| WO | 2016008590 A1 | 1/2016 |
| WO | 2016008690 A1 | 1/2016 |

*Primary Examiner* — Shahdeep Mohammed

(57) ABSTRACT

A system comprises an imaging device for imaging within a body of a patient. The imaging device comprises a flexible elongate member and an imaging assembly disposed at a distal portion of the flexible elongate member. The imaging assembly comprises an array of imaging elements and a plurality of electronic components configured to perform an electrical function associated with imaging within the body of the patient using the array of imaging elements. Each of the plurality of electronic components is radiopaque such that the plurality of electronic components comprises a radiopaque pattern at the distal portion of the flexible elongate member. A method of imaging within a patient body comprises receiving a radiographic image representative of an ultrasound imaging device positioned within the patient body and determining an orientation of the ultrasound imaging device using a radiopaque pattern of a plurality of electronic components in the radiographic image.

16 Claims, 9 Drawing Sheets

(51) Int. Cl.
  *A61B 6/12* (2006.01)
  *A61B 6/46* (2024.01)
  *A61B 8/08* (2006.01)
  *A61B 8/12* (2006.01)
  *A61B 90/00* (2016.01)

(52) U.S. Cl.
  CPC .............. *A61B 8/0883* (2013.01); *A61B 8/12* (2013.01); *A61B 8/445* (2013.01); *A61B 8/463* (2013.01); *A61B 8/5261* (2013.01); *A61B 90/39* (2016.02); *A61B 2090/3966* (2016.02)

(56) References Cited

U.S. PATENT DOCUMENTS

| | | | |
|---|---|---|---|
| 2005/0154293 A1* | 7/2005 | Gisselberg | A61B 5/062 600/420 |
| 2006/0241465 A1 | 10/2006 | Huennekens et al. | |
| 2007/0016071 A1 | 1/2007 | Eberle et al. | |
| 2011/0010925 A1 | 1/2011 | Nix et al. | |
| 2014/0052119 A1* | 2/2014 | Stewart | A61B 18/1492 606/41 |
| 2014/0058494 A1* | 2/2014 | Ostroff | A61N 1/37205 607/122 |
| 2014/0180068 A1 | 6/2014 | Spencer et al. | |
| 2016/0008067 A1* | 1/2016 | Hadjicostis | A61B 8/445 600/439 |
| 2016/0228088 A1 | 8/2016 | Okuno et al. | |
| 2017/0042614 A1* | 2/2017 | Salahieh | A61M 25/1011 |

* cited by examiner

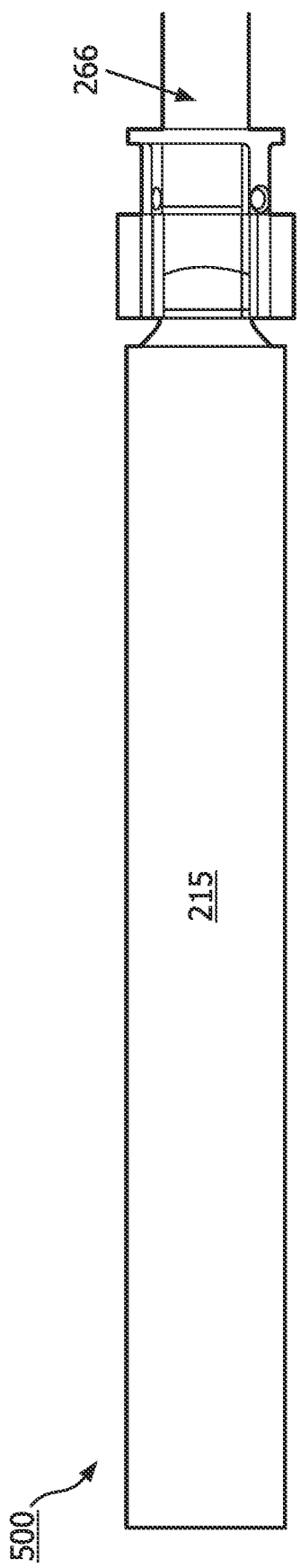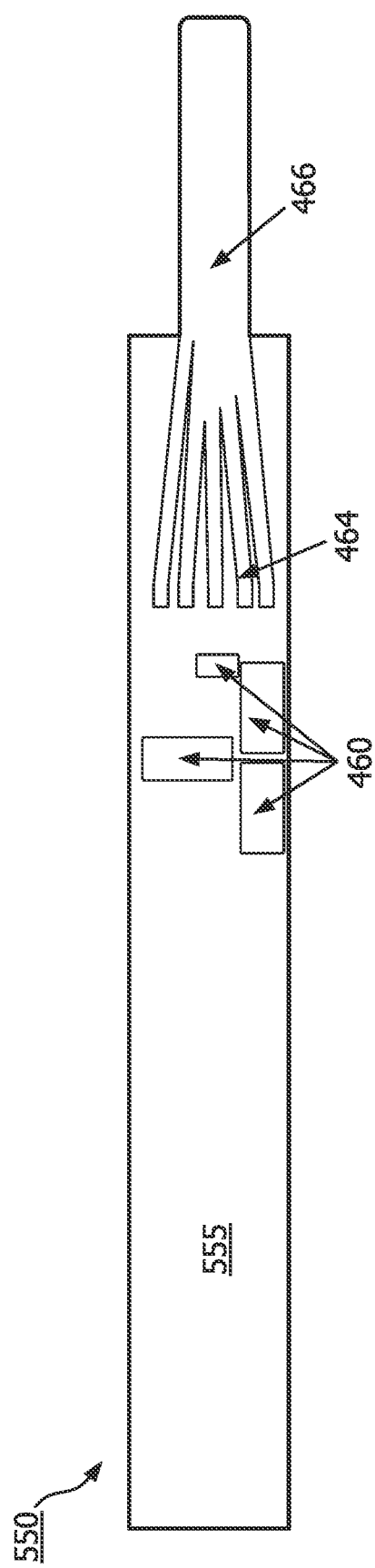

RADIOPAQUE ARRANGEMENT OF ELECTRONIC COMPONENTS IN INTRA-CARDIAC ECHOCARDIOGRAPHY (ICE) CATHETER

RELATED APPLICATIONS

The present application is the U.S. National Phase application under 35 U.S.C. § 371 of International Application No. PCT/IB2017/055829, filed on Sep. 26, 2017, which claims priority to and benefit of U.S. Provisional App. Nos. 62/403,245, filed Oct. 3, 2016, and 62/512,880, filed May 31, 2017, the entireties of which are incorporated by reference herein.

TECHNICAL FIELD

The present disclosure relates generally to devices for imaging within a body of a subject. For example, an intra-cardiac echocardiography (ICE) catheter can include a radiopaque pattern formed of electronic components performing electronic functions related to an array of ultrasound transducers.

BACKGROUND

Diagnostic and therapeutic ultrasound catheters (or guidewires) have been designed for imaging inside many areas of the human body. Ultrasound catheters may be used and adapted for a variety of applications, including intra-cardiac echocardiography (ICE), transesophageal echocardiogram, intervascular imaging, and imaging of other intraluminal or fluid-filled structures.

For example, ICE is emerging as the standard of care for imaging within the heart and surrounding structures, for example, to guide and facilitate transseptal lumen punctures, left atrial appendage closures, atrial fibrillation ablation, and valve repairs. An ICE catheter typically includes an array of transducers at the distal portion of the catheter and a plurality of signal wires connecting the array to an imaging console. The array may be flat, curved, annular or may have any other configuration. The same transducers or separate transducers may be used to generate and receive echoes from the tissue. The signal wires may carry signals to control the array and transmit echo signals to the imaging console. The assembly may provide rotational, 2-way, or 4-way steering mechanisms such that anterior, posterior, left, and/or right views of the heart anatomy may be imaged.

When inserting an ultrasound catheter within the body of a patient to obtain an ultrasonic image, a radiographic image of the body may also be obtained to show where the catheter is located within the body. While the radiographic image helps a user, such as a physician, to locate the catheter within the body, the radiographic image does not indicate the orientation of the catheter. Ultrasound catheters are not configured to allow the radiographic image to indicate which direction the ultrasound array is emitting ultrasonic energy. This limits a doctor's ability to easily relate the radiographic image of the ICE catheter within the body with the ultrasound image of the body obtained by the ICE catheter.

SUMMARY

An ultrasound imaging device, such as an intra-cardiac echocardiography (ICE) catheter, obtains ultrasound images within a patient body. When the ultrasound imaging device is inserted into the body, the clinician needs to know where, inside the body, the imaging device is located. Thus, in parallel with the ultrasound imaging device, a radiographic imaging unit, positioned outside of the patient body, is used to capture an external radiographic, e.g., X-ray image, of the portion of the patient body where the imaging device is inserted. The ultrasound imaging device includes an imaging assembly mounted at a distal portion of the flexible elongate portion of the catheter body. The imaging assembly includes an array of ultrasound transducers as well as electronic circuits for controlling and receiving and transmitting signals using the transducers. Electronic components implemented in the circuits, such as a resistors and/or capacitors include metallic and/or electron dense material that make them radiopaque or visible within a radiographic image. The electronic components can be arranged in a non-symmetric or asymmetric manner at the distal portion of the catheter such that the orientation of the imaging device can be determined using the radiographic image.

Embodiments of the present disclosure provide a system. The system comprises an imaging device for imaging within a body of a patient, comprising: a flexible elongate member configured to be inserted into the body of the patient; an imaging assembly disposed at a distal portion of the flexible elongate member, the imaging assembly comprising: an array of imaging elements; and a plurality of electronic components configured to perform an electrical function associated with imaging within the body of the patient using the array of imaging elements, wherein each of the plurality of electronic components is radiopaque such that the plurality of electronic components comprises a radiopaque pattern at the distal portion of the flexible elongate member.

In some embodiments, the plurality of electronic components comprises passive components. In some embodiments, the plurality of electronic components comprises capacitors. In some embodiments, the plurality of electronic components is mounted on a circuit board disposed adjacent to the array of imaging elements. In some embodiments, the array of imaging elements comprises an outward surface and an inward surface, and the system further comprises: an integrated circuit adjacent to the inward surface of the array of imaging elements. In some embodiments, the integrated circuit comprises a first surface and a second surface opposite the first surface, wherein the first surface of the integrated circuit is coupled to the array of imaging elements. In some embodiments, the imaging assembly further comprises an acoustic backing material comprising a first surface and a second surface opposite the first surface, wherein the second surface of the integrated circuit is coupled to the first surface of the acoustic backing material. In some embodiments, the system further comprises an interconnect board in communication with at least one of the array of imaging elements or the integrated circuit. In some embodiments, the interconnect board is in contact with an acoustic backing material of the imaging assembly. In some embodiments, the integrated circuit is configured to control the array of imaging elements.

In some embodiments, the system further comprises a radiographic imaging unit configured to obtain a radiographic image of the imaging device within the body of the patient; and a computing device in communication with the radiographic imaging unit and configured to determine an orientation of the imaging assembly based on a radiopaque pattern of the plurality of electronic components in the radiographic image. In some embodiments, the radiopaque pattern comprises a non-symmetric shape, wherein the computing device is configured to determine the orientation of the imaging assembly based on the non-symmetric shape of the radiopaque pattern. In some embodiments, the computing device is further configured to co-register imaging data obtained by the imaging device and the radiographic image based on the determined orientation of the imaging assembly. In some embodiments, the computing device is configured to output the co-registered imaging data and the radiographic image to a display. In some embodiments, the computing device is configured to superimpose the imaging data on a corresponding location in the radiographic imaging based on the co-registering. In some embodiments, the imaging device is an intra-cardiac echocardiography device.

Embodiments of the present disclosure provide a method of imaging within a patient body. The method comprises: receiving, at a computing device in communication with a radiographic imaging unit, a radiographic image representative of an ultrasound imaging device positioned within the patient body, the ultrasound imaging device comprising, at a distal portion of a flexible elongate member, an array of transducers and a plurality of electronic components configured to perform an electrical function associated the array of transducers, wherein each of the plurality of electronic components is radiopaque such that the plurality of electronic components comprises a radiopaque pattern at the distal portion of the flexible elongate member; and determining, by the computing device, an orientation of the ultrasound imaging device using the radiopaque pattern of the plurality of electronic components in the radiographic image.

In some embodiments, the method further comprises superimposing an image of the patient body obtained the ultrasound imaging device on the received radiographic image based on the determined orientation of the ultrasound imaging device.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 5A is a bottom view of the imaging assembly of the imaging device, according to aspects of the present disclosure.

FIG. 5B is a graphical representation of a radiographic image of the bottom view of the imaging assembly of FIG. 5A, according to aspects of the present disclosure.

DETAILED DESCRIPTION

Figure 1:
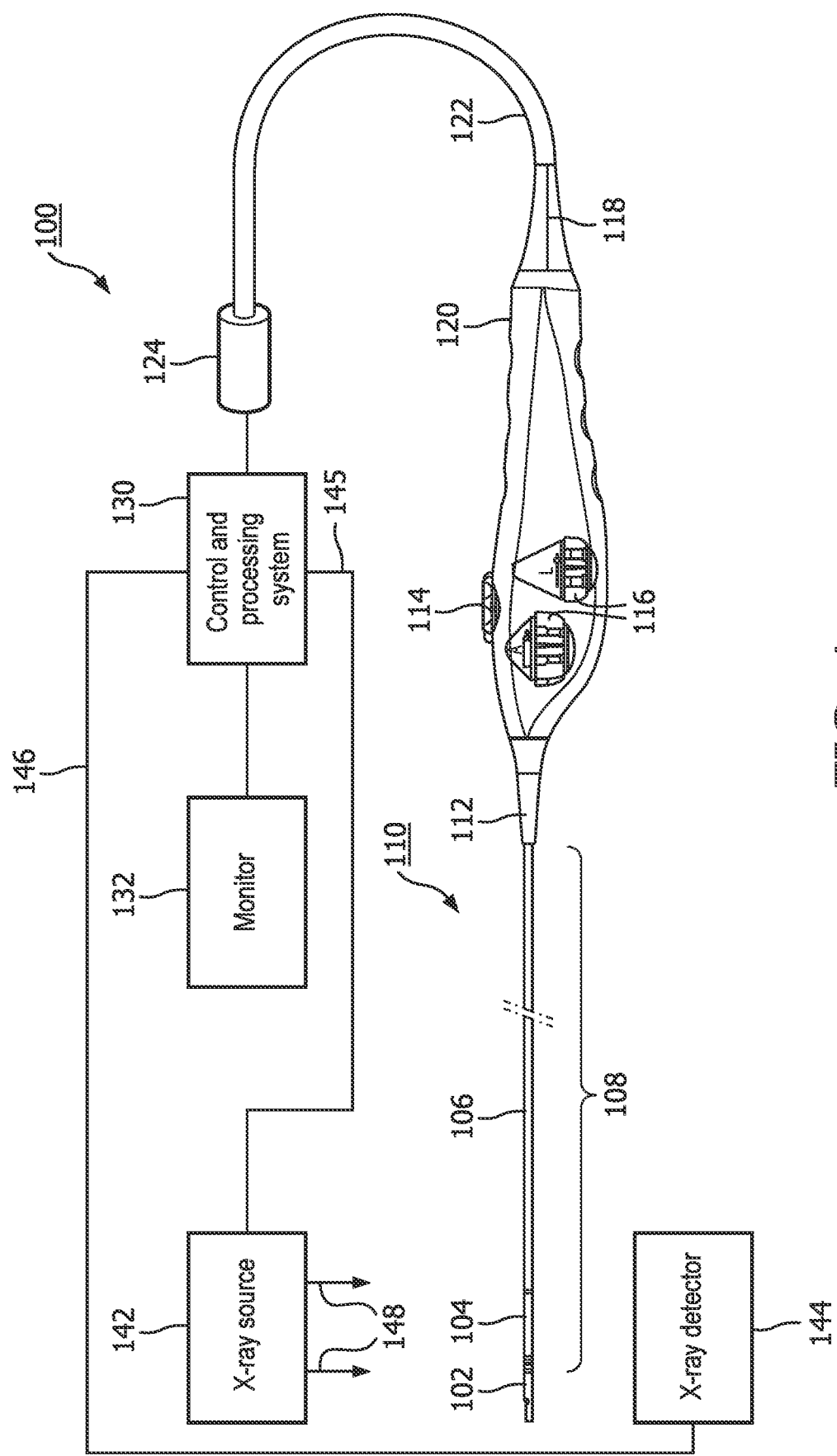
FIG. 1 is a schematic diagram of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system may be described in terms of imaging fluid filled structures, it is understood that it is not intended to be limited to this application and for example it can be used for imaging within a body of a patient. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In some embodiments, a radiographic or X-ray image may be used to provide information about anatomy of patient or the position of a device within the anatomy. Radiographic images can include fluoroscopy or angiography. Fluoroscopy can include, for example, moving radiographic images obtained without contrast media within the anatomy. Angiography can include still radiographic images obtained with contrast media within the anatomy. On its own, a 2D radiographic image can provide an attenuation map associated with X-ray transmission through the body, without any depth information. That is, radiography is able to provide useful information where there are significant changes in the attenuation of the X-ray as it passes through the patient—either as a consequence of the different amounts of tissue between the source and the detector or as a consequence of the introduction of a radiopaque medium such as contrast agent or because of inserting devices having radiopaque material into the body. In some instances, the present disclosure refers to a radiographic image as a silhouette, referencing the silhouette appearance of objects within the radiographic image.

Combining radiographic information with some other form of image information (e.g., ultrasound image data obtained within the patient body) can be diagnostically helpful. For example, 2D or 3D ultrasound imaging data can augment the radiographic image with a more complete view of the patient anatomy. During procedures associated with the structure or function of the chambers of the heart, it may be necessary to obtain an image of the anatomy of the heart using an intra-cardiac echocardiography (ICE) catheter. The ultrasound imaging data obtained by the ICE catheter from within the heart can be combined with a radiographic image.

In some examples, an imaging assembly coupled to a distal portion of an ICE catheter may include imaging transducer array and an integrated circuit (IC) coupled to the imaging element. The imaging assembly may include a 1D or 2D ultrasound transducer array. The IC is configured to process signals received from the imaging elements. In some embodiments, the IC may convert the signals received by the imaging elements into electrical signals, and then amplify and beamform the electrical signals. The IC may be connected to an imaging system for further processing of the signals. The IC may further include one or more electronic components, e.g., passive components, that can be used as radiopaque markers to track the catheter tip and determine the orientation of the device with use of an external imaging modality (e.g. fluoroscopy or angiography).

The integrated circuit (IC) may be present at the tip of the catheter to interface with the ultrasound transducer array and may be used to command the ultrasound transducer array. Some electronic components, e.g., passive components, related to commanding the ultrasound transducer array may have a dimension too large to fit within the IC itself. That is, the electronic components may not be formed within the IC itself. The electronic components may be in electrical communication with the IC. The electronic components can be electrically and/or mechanically coupled to a circuit board. For example, the electronic components can be soldered to the circuit broad. The passive components may have to be in close proximity to the IC but their exact orientation and position may not be important. The passive components also have electron dense materials that render them radiopaque. As such, they are easily visible under X-ray. Furthermore, the shape of the passive components is well defined with electron dense material filling the whole space of the passive component. As such their profile is also easily discernible. In some examples, in the radiographic image, the passive components may produce an axially asymmetric silhouette at the distal end of the imaging assembly.

An ultrasound imaging assembly may include imaging elements such as ultrasound transducers as well as control and interface circuits for controlling transducers as well as receiving and transmitting signals. As noted, some electronic components of the control and interface circuits may have a large dimension. The large dimensional electronic components may include radiopaque material such that the imaging assembly can easily be recognized against a background image of the body in a radiographic image. The large dimensional electronic components can be passive or active electronic components. For example, the electronic components can be resistors and/or capacitors having metallic and/or electron dense material that make them radiopaque. These large dimensional electronic components may be mounted in a predetermined mounting arrangement such that because of their mounting arrangement, not only their location, but also their orientation may be recognized in the radiographic image.

Embodiments of the present disclosure implement a plurality of electronic components at the distal portion of an imaging device. The electronic component may perform an electrical function associated with ultrasound imaging within the body of the patient. The electronic component may also include radiopaque material such that the plurality of electronic components may create a radiopaque pattern at the distal portion of the flexible elongate member when viewed in a radiographic image.

In some embodiments, the tip of the ICE catheter can be made up of a two dimensional ultrasound transducer array mounted directly on an IC. The IC provides a way to transmit and receive on any of the elements of the 2D transducer array via a much smaller number of control lines. The IC may also provide amplification for the receive signals and electrical impedance matching between the individual elements and the micro-cable that interconnects the IC to the rest of the ultrasound imaging system. To ensure proper functionality of the IC when it is located at the end of a micro-cable, bypass capacitors are required. The bypass capacitors serve to reduce the effect of any electrical noise on the interconnects running the length of the catheter and also provide some amount of back-up charge if the voltage should drop on the supply lines to the IC. For a bypass capacitor to be effective it is necessary to have a relatively large value. As such these components may be large compared to the IC. Capacitors are made up of two electrode plates that are separated by a dielectric material. In order to achieve the capacitance value required, the plates/electrodes of the capacitor are large; to fit them into the packaging of the capacitor it is necessary that the plates and dielectric are very thin such that they can be folded or wrapped into the available space. The benefit of this folding is that it provides a package that is completely filled with electron dense (the plate electrode) material which then provides the radiodensity necessary to be visualized under fluoroscopy.

The embodiments described herein provide numerous advantages. Complicated surgeries are more frequently accomplished using minimally invasive procedures. Key to minimally invasive procedures is the ability to provide quality images within the body to assess, monitor, or guide the intervention. Thus, when the device provides an image within the body of the patient, a user of the system needs to know the orientation of the device within the body. By knowing the orientation of the device, the user may know the received image belongs to which portion of the body. For example, the silhouette of electronic components of the ultrasound imaging device can be asymmetrically positioned at the distal portion of the flexible elongate body so that the left side, right side, top, bottom, and/or combinations thereof are distinguishable from another in the radiographic image. Because the direction the ultrasound transducer array emits ultrasound energy is known, the system and/or a user can identify the imaged anatomy based on the orientation of the ultrasound transducer array determined from the radiographic imaging.

FIG. 1 is a schematic diagram of an imaging system 100, according to embodiments of the present disclosure. The system 100 that can be used for imaging within a body of a patient may include an imaging device 110, a connector 124, a control and processing system 130, such as a console and/or a computer, and a monitor 132. In some examples, the imaging device 110 is an intra-cardiac echocardiography device (ICE). The imaging device 110 includes an imaging assembly 102 at the tip of a flexible elongate member 108, and a handle 120. The imaging assembly 102 can include one or more ultrasound transducer elements, such as an array of ultrasound transducers, and associated electronic circuitry. In some embodiments, the imaging system 100 is used for generating 2D and/or 3D images. For example, the imaging assembly can include a 1D imaging array for 2D imaging or a 2D imaging array for 3D imaging. In some examples, the imaging system 100 is used for generating x-plane images at two different viewing directions perpendicular to each other. The transducer elements and/or electronic circuitry can be referenced as an imaging core or imaging assembly in various embodiments.

The flexible elongate member 108 includes a distal portion 104 and a proximal portion 106. The imaging assembly 102 can be directly or indirectly coupled to the distal portion 104 of the flexible elongate member 108. For example, the imaging assembly 102 can be positioned within a tip member (e.g., tip member 200 of FIG. 2) and the tip member can be coupled to the distal portion 104 of the flexible elongate member 108. The imaging assembly 102 can extend a length of the flexible elongate member 108, such as the length of the distal portion 104. The proximal end of the proximal portion 106 is attached to the handle 120, for example, by a resilient strain reliever 112, for manipulation of the imaging device 110 and manual control of the imaging device 110. The handle 120 can include actuators 116, a clutch 114, and/or other steering control components for steering the imaging device 110 in one or more directions, such as by deflecting the imaging assembly 102 and the distal portion 104.

The handle 120 is connected to the connector 124 via another strain reliever 118 and a connection cable 122. The connector 124 may be configured in any suitable configurations to interconnect with the control and processing system 130 and the monitor 132 for processing, storing, analyzing, manipulating, and displaying data obtained from signals generated by the imaging core at the imaging assembly 102. The control and processing system 130 can include one or more processors, memory, one or more input devices, such as keyboards and any suitable command control interface device. The control and processing system 130 can be operable to facilitate the features of the imaging system 100 described herein. For example, the processor can execute computer readable instructions stored on the non-transitory tangible computer readable medium. The monitor 132 can be any suitable display device, such as liquid-crystal display (LCD) panel or the like.

In operation, a physician or a clinician may advance the flexible elongate member 108 to the heart via one or more vessels of the body. The physician or clinician can steer the flexible elongate member 108 to a position near the area of interest to be imaged by controlling the actuators 116 and the clutch 114 on the handle 120. For example, one actuator 116 may deflect the imaging assembly 102 and the distal portion 104 in a left-right plane and the other actuator 116 may deflect the imaging assembly 102 and the distal portion 104 in an anterior-posterior plane. The clutch 114 provides a locking mechanism to lock the positions of the actuators 116 and in turn the deflection of the flexible elongate member while imaging the area of interest.

The imaging process may include activating the ultrasound transducer elements on the imaging assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the control and processing system 130 where the ultrasonic image is reconstructed and displayed on the monitor 132. In some embodiments, the control and processing system 130 can control the activation of the ultrasound transducer elements and the reception of the echo signals. In some embodiments, the control and processing system 130 and the monitor 132 may be part of the same system.

The system 100 may be utilized in a variety of applications such as transseptal lumen punctures, left atrial appendage closures, atrial fibrillation ablation, and valve repairs.

Generally, the system 100 can be used to image vessels, structures, lumens, and/or any suitable anatomy/tissue within a body of a patient including any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the imaging device 110 may be may be used to examine man-made structures such as, but without limitation, heart valves, stents, shunts, filters and other devices. For example, the device 110 can be positioned within fluid filled or surrounded structures, both natural and man-made, such as within a body of a patient. The vessels, structures, lumens, and anatomy/tissue can include a blood vessel, as an artery or a vein of a patient's vascular system, including cardiac vasculature, peripheral vasculature, neural vasculature, renal vasculature, and/or any suitable lumen inside the body.

The system 100 is suitable for use with any catheterization procedure. In addition, the imaging assembly 102 may include any suitable physiological sensor or component for diagnostic, treatment, and/or therapy. For example, the imaging assembly can include an imaging component, an ablation component, a cutting component, a morcellation component, a pressure-sensing component, a flow-sensing component, a temperature-sensing component, and/or combinations thereof. In some examples, the system 100 may be described in the context of intraluminal imaging procedures.

In some embodiments, the system 100 includes an X-ray source 142 and an X-ray detector 144. The X-ray source 142 may generate X-rays 148 that after passing through a body, e.g., a body of the patient, may be captured by the X-ray detector 144. The X-ray detector 144 may generate detection signals and send the signals through the connection 146 to the control and processing system 130. The control and processing system 130 may use the X-ray detected signals to generate a radiographic image of the body and display it on the monitor 132. The control and processing system 130 may further command the X-ray source 142 through the connection 145 and control when the X-ray source 142 is activated. In some examples, the control and processing system 130 activates the X-ray source 142 when the imaging device 110 is within the body of a patient and the radiographic image of the body may include a silhouette of the imaging device 110. The X-ray source 142 and an X-ray detector 144 can be part of a fluoroscopic and/or angiographic imaging device.

Figure 2:
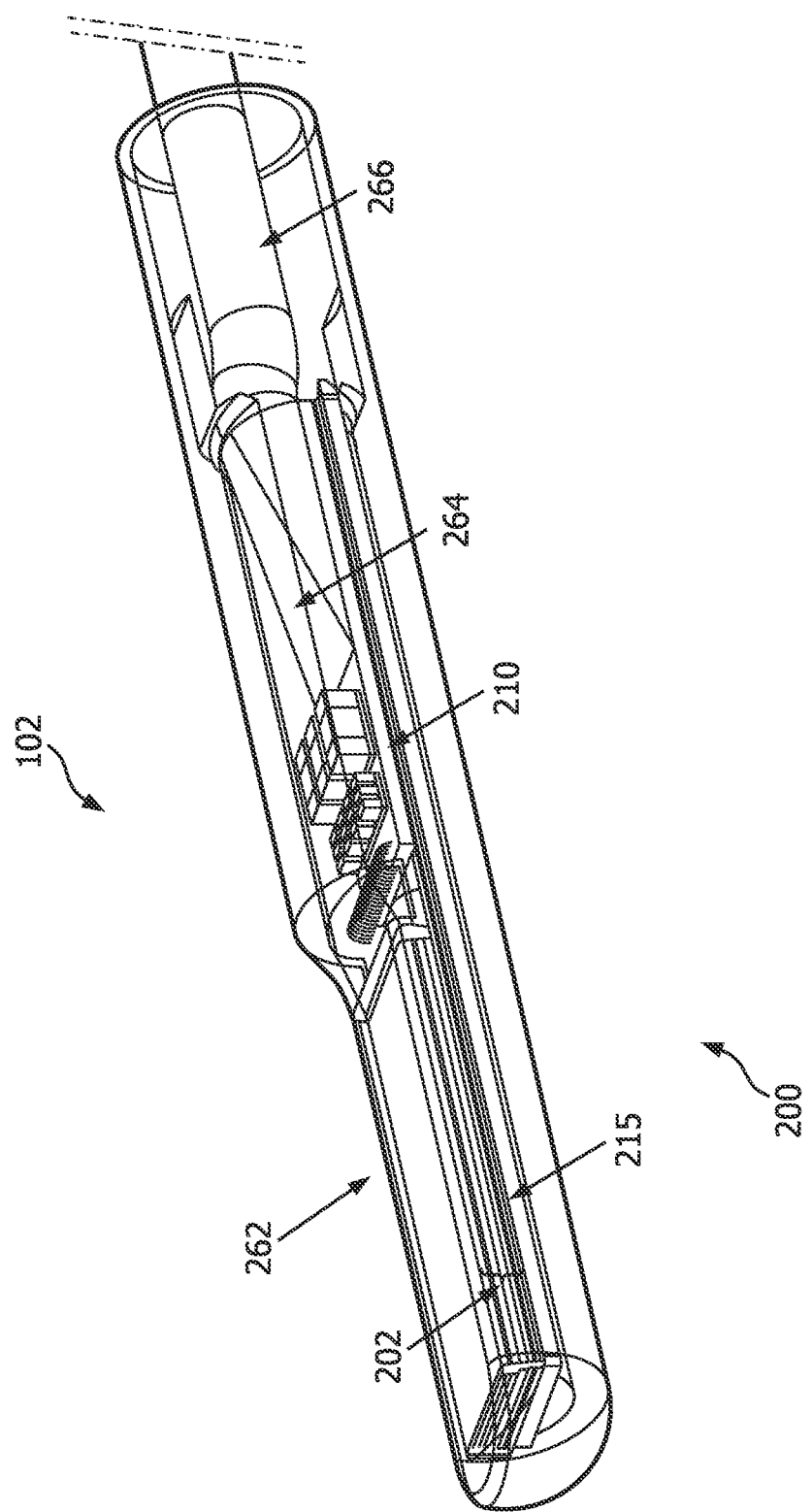
FIG. 2 is a perspective view of an imaging assembly of an imaging device, according to aspects of the present disclosure.

FIG. 2 is a perspective view of the imaging assembly 102, according to embodiments of the present disclosure. In some examples, the distal portion 104 comprises the imaging assembly 102, or the imaging assembly 102 may be coupled to the distal portion 104 of the imaging device 110. The imaging assembly 102 may include the imaging core 262, having an array of ultrasound transducers and associated circuitry, disposed within a tip member 200. The tip member 200 may be a housing for the imaging assembly 102 and include an acoustic window through which ultrasonic energy and reflected echoes propagate. The imaging assembly 102 can be disposed within the tip member 200, and the tip member 200 can be coupled to the distal portion 104 of the flexible elongate member 108. The material type and the wall thickness of the tip member 200 are selected to minimize acoustic distortion, attenuation, and/or reflection. The tip member 200 can also include other features, for example, a guidewire lumen, holes, or other geometry to accommodate additional devices or features such as pressure sensors, drug delivery mechanisms, and/or any suitable interventional features. The tip member 200 may be an optically and/or acoustically translucent cover for the imaging assembly 102. The imaging assembly 102 includes the interconnect board 210 in electrical communication with the imaging core 262. The imaging core 262 is coupled to the electrical cable 266 via the electrical interconnection 264 and the interposer, e.g., the interconnect board 210. The electrical cable 266 can extend from the distal portion 104 proximally through the flexible elongate member 108 and the imaging device 110 to the connector 124, as shown in FIG. 1. In some examples, the imaging assembly 102 includes at least a layer of backing material, e.g., backing layer 215 that may extend under the imaging core 262 and the interconnect board 210. In some embodiments, the diameter of the distal portion of the imaging device may be between 2 mm and 3 mm and the thickness of the distal portion can be about 1 mm. The direction that ultrasound energy propagates from the array of imaging elements 202 is known relative to the other components of the imaging assembly 102, including the interconnect board 210.

In some embodiments, the imaging core 262 of the imaging assembly 102 includes an array of imaging elements or ultrasound transducers 202. For example, acoustic imaging elements 202 may be of any suitable type, including lead zirconate titanate (PZT), piezoelectric or capacitive micromachined ultrasonic transducer (PMUT or CMUT). In some embodiments, the array imaging elements 202 includes plurality of layers, such as a PZT layer, one or more electrode layers, one or more matching layers, etc. In some examples, the array of imaging elements 202 can be in the form of an array of more than 800 imaging elements. In this regard, the imaging elements 202 may be arranged in a 2-dimensional array having a same length and a same width such that the array of imaging elements 202 may have a symmetrical aperture. In some examples, the imaging elements 202 may be arranged in a 2-dimensional array having a length greater than a width such that more imaging elements 202 extend along the length of the array than across the width. As a result, the array of imaging elements may have an asymmetrical aperture.

Figure 3:
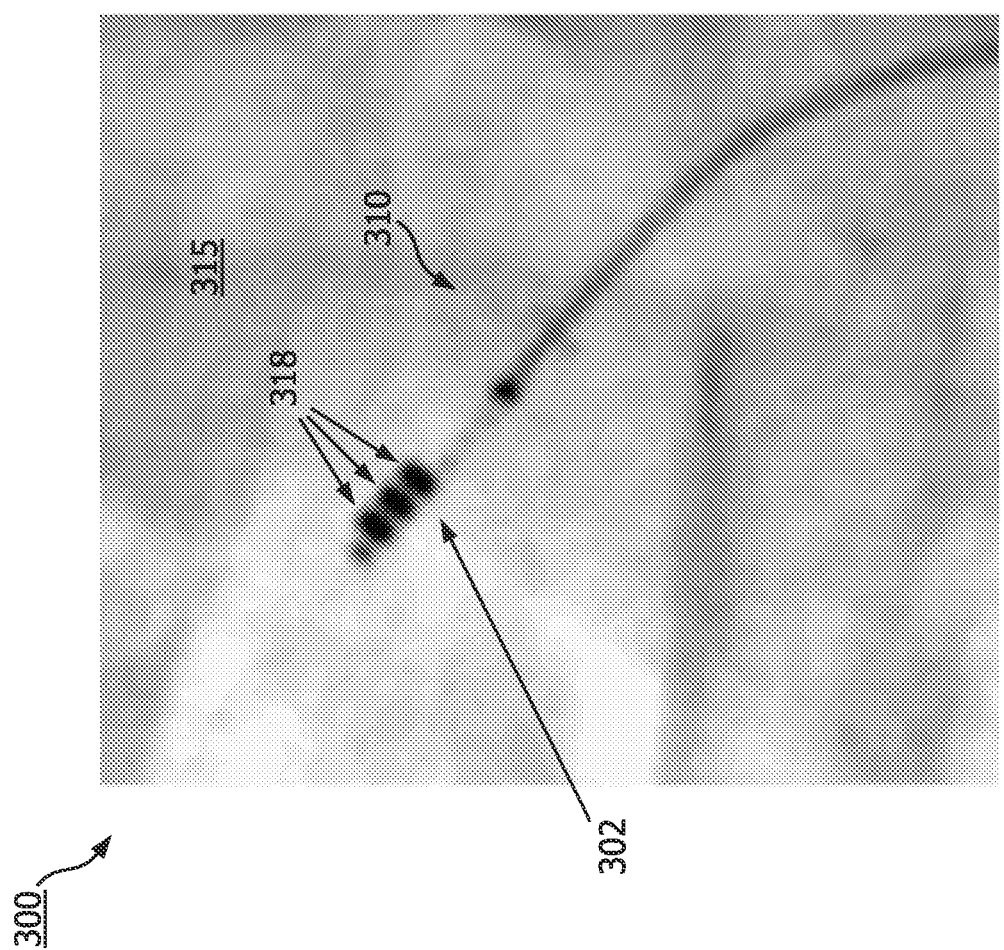
FIG. 3 is a radiographic image of the imaging device in a body.

FIG. 3 is a radiographic image 300 of the imaging device in a body. The radiographic image 300 includes a silhouette 310 of the imaging device 110 and a silhouette 302 of the imaging assembly 102 inside a body 315 of a patient, for example. The radiographic image 300 also shows silhouette 318 of radiopaque material of the imaging assembly 102. For example, the radiopaque material of the imaging assembly 102 can include three electronic components, such as capacitors, associated with the imaging assembly 102.

The system 100 can receive the radiographic image 300 of the imaging device 110 within the body 315 of the patient obtained by a radiographic imaging unit, e.g., the X-ray source 142 and the X-ray detector 144. Also, a computing device, e.g., the control and processing system 130 may also be in communication with the radiographic imaging unit and to determine an orientation of the imaging assembly 102 based on a radiopaque pattern of the plurality of electronic components 318 in the radiographic image 300.

In some examples, the radiopaque pattern may include a non-symmetric shape, such that the computing device 130 may determine the orientation of the imaging assembly 102 based on the non-symmetric shape of the radiopaque pattern. In some examples, the computing device 130 may co-register imaging data obtained by the imaging device 110 and the radiographic image based on the determined orientation of the imaging assembly 102.

In some embodiments, the computing device 130 may output the co-registered imaging data and the radiographic image to the display, e.g., monitor 132. In some examples, the computing device 130 may superimpose the imaging data on a corresponding location in the radiographic imaging based on the co-registering.

Figure 8A:
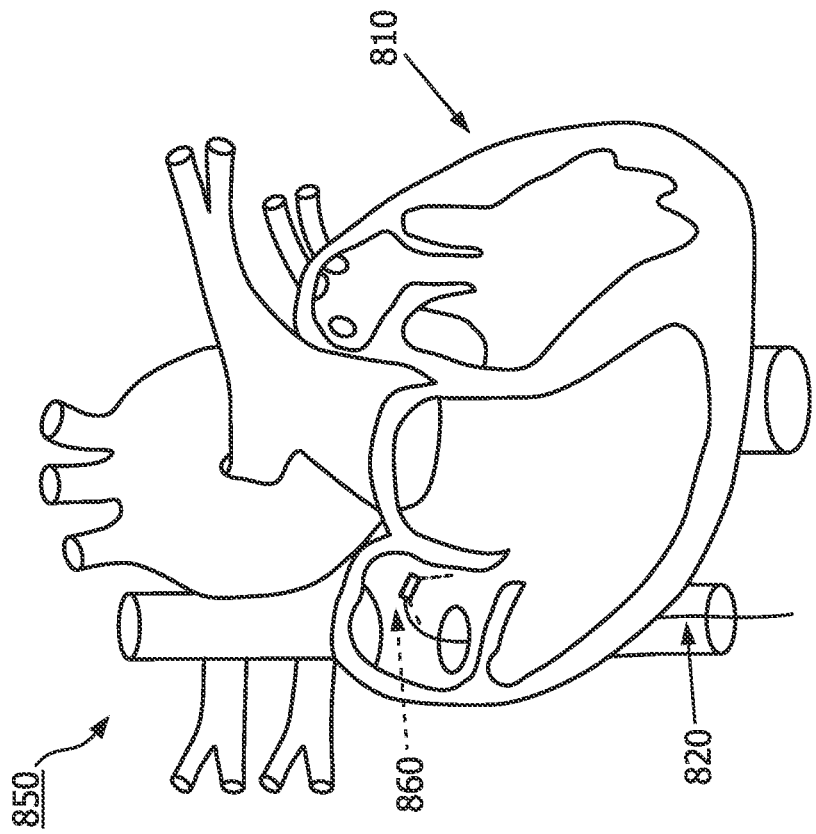
FIG. 8A is a diagram showing a body organ and the imaging device inside the body organ, according to aspects of the present disclosure.
Figure 8B:
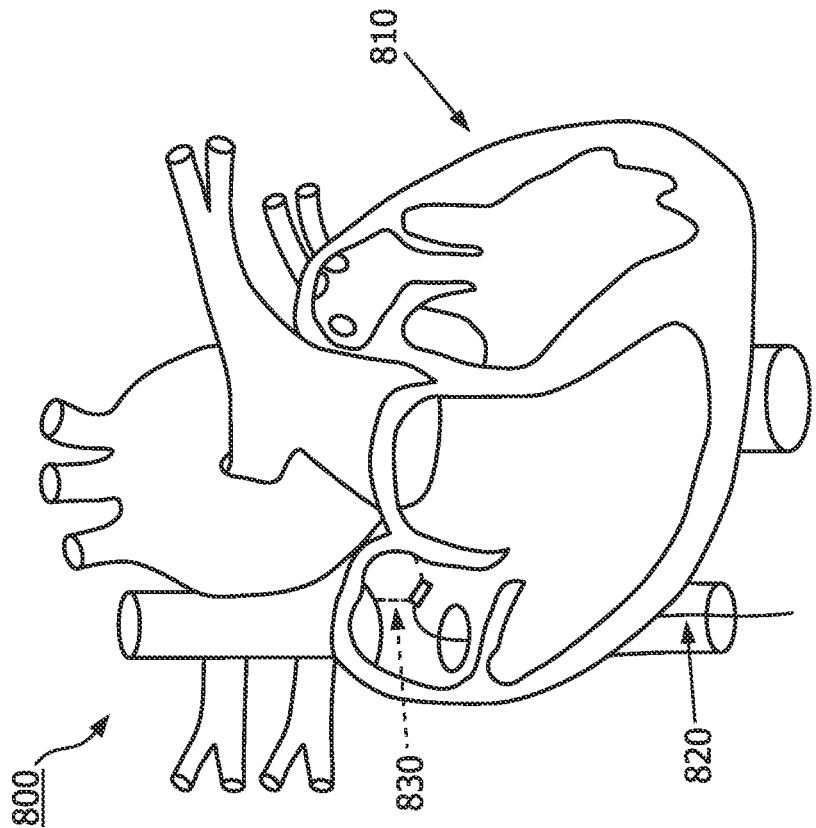
FIG. 8B is a diagram showing the body organ and the imaging device inside the body organ, according to aspects of the present disclosure.

In some examples, the computing device 130 may receive a 2D or 3D image of a lumen in the body from the imaging device 110. Then the computing device 130 may superimpose the received 2D or 3D image on the received radiographic image. In some embodiments, a focusing direction of the imaging assembly may be indicated on the superimposed image. In some examples, the focusing direction may be indicated on the silhouette image of the imaging assembly as shown in FIGS. 8A and 8B.

Figure 4A:
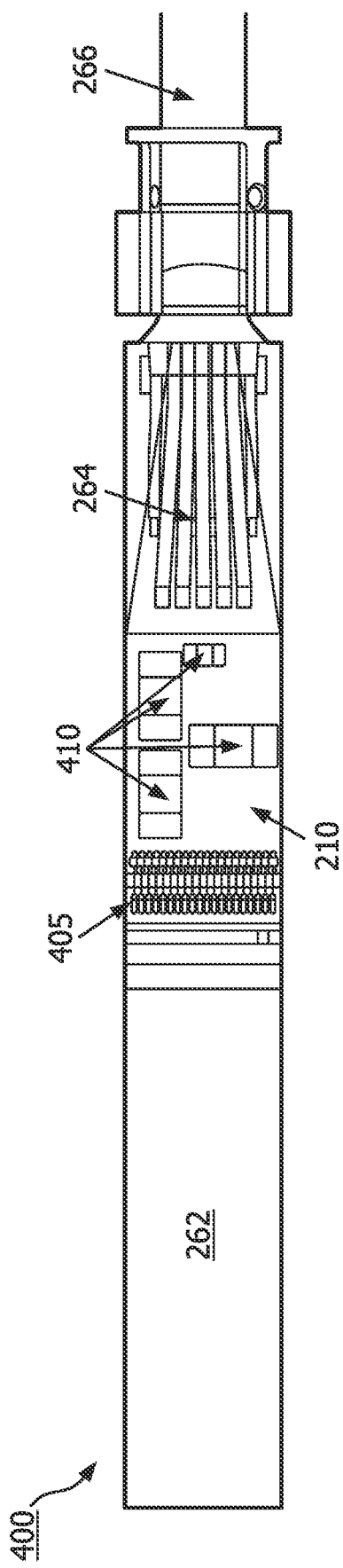
FIG. 4A is a top view of the imaging assembly of the imaging device, according to aspects of the present disclosure.

FIG. 4A is a top view 400 of the imaging assembly 102 of the imaging device 110, according to aspects of the present disclosure. The top view 400 includes the imaging core 262 adjacent to an interface board, e.g., the interconnect board 210. Also shown are the electrical interconnection 264 and electrical cable 266. The top view 400 further includes electronic components 410 mounted on the interconnect board 210. In some examples, the electronic components 410 are surface mounted on the interconnect board 210. In some examples, the plurality of electronic components 410 may perform an electrical function associated with imaging within the body of the patient using the array of imaging elements 202 of the imaging core 262. In some examples, each of the plurality of electronic components 410 is radiopaque such that the plurality of electronic components 410 creates a radiopaque pattern at the distal portion 104 of the flexible elongate member 108. In some embodiments, the plurality of electronic components 410 are mounted on a circuit board, e.g., the interconnect board 210, adjacent to the array of imaging elements 202.

FIG. 4A illustrates that the interconnect board 210 or circuit board 210 includes one or more electronic components 410. In the illustrated embodiment, a plurality of electronic components 410 is shown. It is understood that the plurality of electronic components 410 can include one, two, three, four, five, six, seven, eight, or more electronic components in various embodiments. The electronic components 410 can be active electronic components, passive electronic components, and/or a combination of active and passive electronic components. Active electronic components can include semiconductor components, diodes, transistors, integrated circuits, optoelectronic devices, etc. Passive electronic components can include resistors, capacitors, magnetic/inductive devices, memristors, transducers, sensors, detectors, thermocouple/thermopile, thermistor, antennas, etc. The electronic components are in electrical communication with one or more components of the imaging assembly 102 and are configured to electrically interact with the imaging assembly 102 in some manner facilitating the imaging and/or otherwise associated with imaging within the body of the patient. For example, the electronic components can be configured to perform an electrical function associated with using the imaging array 202 to obtain imaging data within the body of the patient. For example, capacitor(s) can be used to reduce the effect of any electrical noise on the electrical interconnects running the length of the catheter. This can facilitate an improved imaging quality. For example, the one or more capacitors can store an electrical charge to provide some amount of back-up charge if the voltage should drop on the supply lines to the IC. This can facilitate powering the transducers of the imaging array 202 to emit ultrasound energy into the body of the patient. For example, a thermistor on the interconnect board 210 can indicate the temperature of the imaging assembly 102. This allows for ensuring that the imaging device 110 does not increase the temperature within the blood vessel too much.

In some embodiments, the radiographic image of the electronic components 410 provides a two dimensional image representing the cumulative radio opacity of the electronic components as well as the body tissues being imaged. The one or more electronic components 410 can be arranged such that a radiographic image of the imaging assembly conveys information about the orientation of the imaging assembly 102, such as which direction ultrasound energy is being emitted into the body. For example, the control and processing system 103 can determine, based on the arrangement of electronic components 410, whether the radiographic image is showing a top view, bottom view, left side view, right side view, and/or a combination thereof, of the imaging assembly 102. Accordingly, the orientation of the imaging assembly 102 within the body may be recognized from the radiographic image.

In some embodiments, the electronic components, e.g., the large dimensional electronic components 410 of the imaging assembly 102 may be arranged such the electronic components collectively have a non-symmetrical footprint. In some examples, the non-symmetrical footprint is predesigned such that in a radiographic image of the imaging assembly a top view (focusing up) of the imaging assembly may easily be recognized from a bottom view (focusing down) of the imaging assembly. In some examples, a recognition program executing on the control and processing system 103 may recognize the top view from the bottom view.

In some embodiments, the electronic components, e.g., the large dimensional electronic components 410 of the imaging assembly 102 may be arranged such the electronic components collectively have a non-symmetrical shape in a direction vertical to the footprint. In some examples, the non-symmetrical vertical shape is predesigned such that in a radiographic image of the imaging assembly a left side view (focusing right) of the imaging assembly may easily be recognized from a right side view (focusing left) of the imaging assembly. In some examples, a recognition program executing on the control and processing system 103 may recognize the left side view from the right side view.

The non-symmetrical arrangement allows for a user and/or the control and processing system 103 to distinguish between the top view, bottom view, left side view, right side view, and/or a combination thereof. In some embodiments, each individual electronic component 410 can be non-symmetric. In some embodiments, individual electronic components 410 can be symmetric, such as a square, rectangle, or circle, but the plurality of electronic components 410 can be arranged in a non-symmetric manner.

In some embodiments, the array of imaging elements 202 comprises an outward surface and an inward surface and the system 100 further includes an integrated circuit 204 adjacent to the array of imaging elements 202. In some examples, the integrated circuit 204 may include a first surface and a second surface opposite the first surface such that the first surface of the integrated circuit 204 is coupled, e.g., flip chipped, to the array of imaging elements 202. In some examples the interconnect board 210 and the integrated circuit 204 are part of a monolithic substrate. In some examples, the interconnect board 210 and the integrated circuit 204 are coupled through wire bonds 405.

In some embodiments, the imaging assembly 102 further includes an acoustic backing material 215 that may include a first surface and a second surface opposite the first surface. The second surface of the integrated circuit 204 is coupled to the first surface of the acoustic backing material 215. In some embodiments, the interconnect board 210 is in communication with at least one of the integrated circuit 204 or the array of imaging elements 202. In some examples, the interconnect board 210 is in contact with the layer of acoustic backing material 215 of the imaging assembly 102. Additionally, The presence of the electronic components, e.g., passive components 410, in the distal portion of the device and their placement and alignment means that the fluoroscopic image of the device is readily visible and the orientation of the device readily discernible. As such the location and orientation of the imaging assembly can be co-registered with the fluoroscopy system such that the ultrasonic image from the ICE catheter can be overlaid on the fluoroscopic image. Also, the layout of the components may take various configurations. The positions may be optimized so as to create unique silhouettes for any orientation or rotation of the imaging device.

Figure 4B:
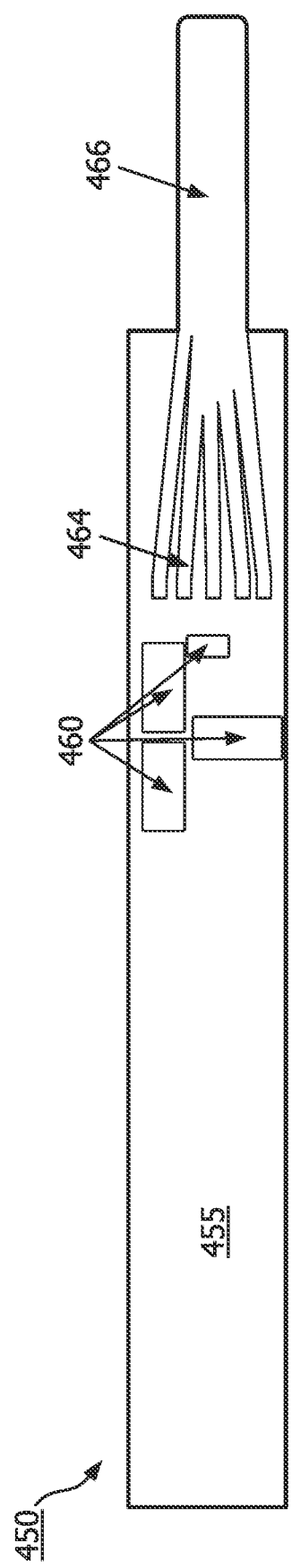
FIG. 4B is a graphical representation of a radiographic image of the top view of the imaging assembly of FIG. 4A, according to aspects of the present disclosure.

FIG. 4B is a top view 450 of a simulated radiographic image of the imaging assembly of an imaging device, according to aspects of the present disclosure. In some examples, the view 450 is a simulated silhouette, e.g., simulated radiographic image of the imaging assembly 102. In the view 450, the components having more radiopaque material are darker. In some examples, the view 450 shows a layer 455 that includes the silhouette images of the backing layer 215 and the layers on top of the backing layer. In some examples, the view 450 also shows the silhouette images 460 of the electronic components 410, the silhouette images 466 of the electrical cable 266, and the silhouette images 464 of the electrical cable 264.

FIG. 5A is a bottom view 500 of the imaging assembly 102 of the imaging device 110, according to aspects of the present disclosure. The bottom view 500 may include the backing layer 215 that may extend under the imaging core 262 and the interconnect board 210. Also shown is the electrical cable 266.

FIG. 5B is a bottom view 550 of a simulated radiographic image of the imaging assembly of an imaging device, according to aspects of the present disclosure. In some examples, the view 550 is a simulated silhouette, e.g., simulated radiographic image of the imaging assembly 102. As noted, in the view 550, the components having more radiopaque material are darker. In some examples, the view 550 shows a layer 555 that includes the silhouette images of the backing layer 215 and the layers on top of the backing layer. In some examples, the view 550 also shows the silhouette images 460 of the electronic components 410, the silhouette images 466 of the electrical cable 266, and the silhouette images 464 of the electrical cable 264. Because of the non-symmetric arrangement of the electronic components 410, the top view of FIG. 4B is distinguishable from the bottom view of FIG. 5B.

In some embodiments, a radiographic imaging unit with the X-ray source 142 on the top and the X-ray detector 144 on the bottom is used for obtaining the images 450 and 550 of FIGS. 4B and 5B such that the X-rays travel from top to bottom in a way that they impinge from front to the body and emerge from the back of the body. In some embodiment, as shown in FIGS. 4A and 5A, the electronic components 410 have an asymmetric configuration, e.g., footprint, with respect to the right-left sides of the imaging assembly as viewed from top. As the result of this asymmetry, the silhouette images 460 of FIGS. 4B and 5B are not symmetrical with respect to the top-down of the images 450 and 550. Thus, in some examples, when a radiographic image similar to the image 450 shown in FIG. 4B is obtained, based on the configuration of the silhouette images 460, as compared to the electronic components 410 of FIG. 4A, it may be concluded that the imaging assembly 102 is focusing up. In some examples, when a radiographic image similar to the image 550 shown in FIG. 5B is obtained, based on the configuration of the silhouette images 460 as compared to the electronic components 410 of FIG. 5A, it may be concluded that the imaging assembly 102 is focusing down. In some embodiments, the control and processing system 103 may distinguish between the configuration of the silhouette images 460 in FIGS. 4B and 5B and recognize if the imaging assembly is focusing up or down.

Figure 6A:
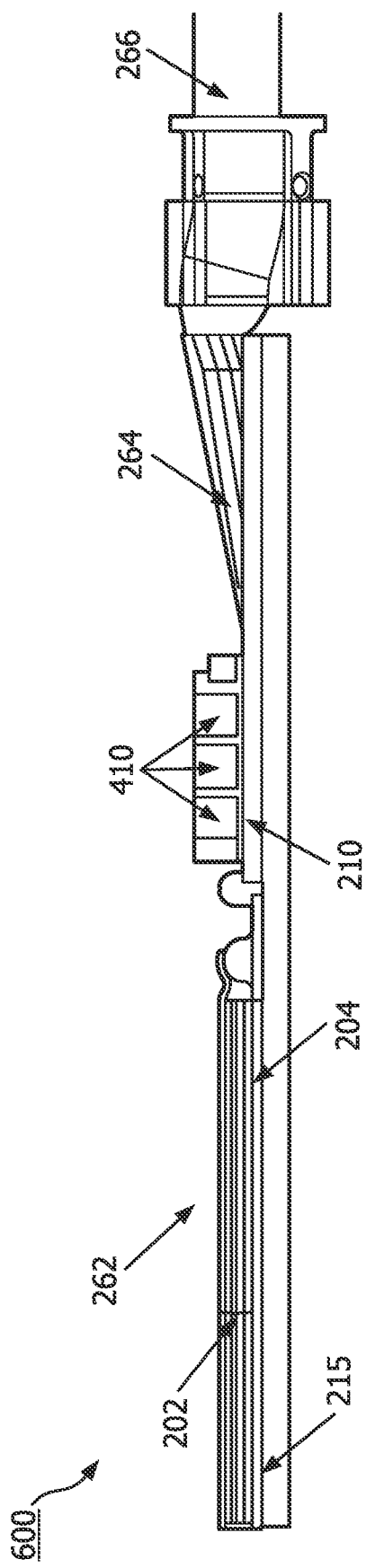
FIG. 6A is a left side view of the imaging assembly of the imaging device, according to aspects of the present disclosure.

FIG. 6A is a left side view 600 of the imaging assembly of the imaging device, according to aspects of the present disclosure. With respect to FIGS. 6A, 6B, 7A, and 7B, the left and right sides are determined/defined with respect to a viewer viewing from the proximal portion of the catheter (e.g., imaging device 110) to the distal portion of the catheter. The left side view 600 includes the imaging core 262 adjacent to the interconnect board 210. Also shown are the electrical interconnections 264 and electrical cable 266. The left side view 600 further includes electronic components 410 mounted on the interconnect board 210. In some examples, the imaging assembly 102 includes a backing layer 215.

Figure 6B:
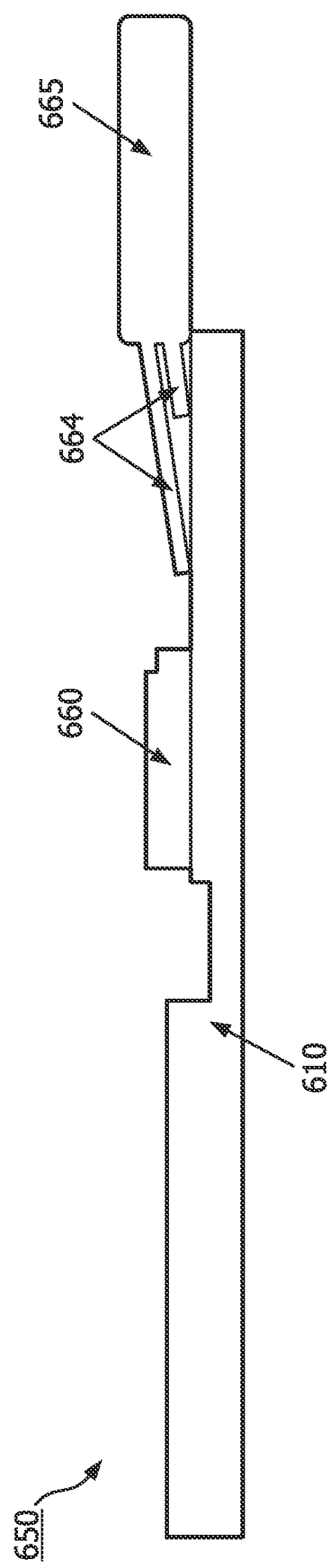
FIG. 6B is a graphical representation of a radiographic image of the left side view of the imaging assembly of FIG. 6A, according to aspects of the present disclosure.

FIG. 6B is a left side view 650 of a simulated radiographic image of the imaging assembly of an imaging device, according to aspects of the present disclosure. In some examples, the view 650 is a simulated silhouette, e.g., radiographic image of the imaging assembly 102. Also in the side views including the side view 650, the material having more radiopaque material is darker. In some examples, the view 650 shows a layer 610 that includes the silhouette images of the backing layer 215 and the layers on top of the backing layer. In some examples, the view 650 also shows the silhouette images 660 of the electronic components 410, the silhouette images 665 of the electrical cable 266, and the silhouette images 664 of the electrical cable 264.

Figure 7A:
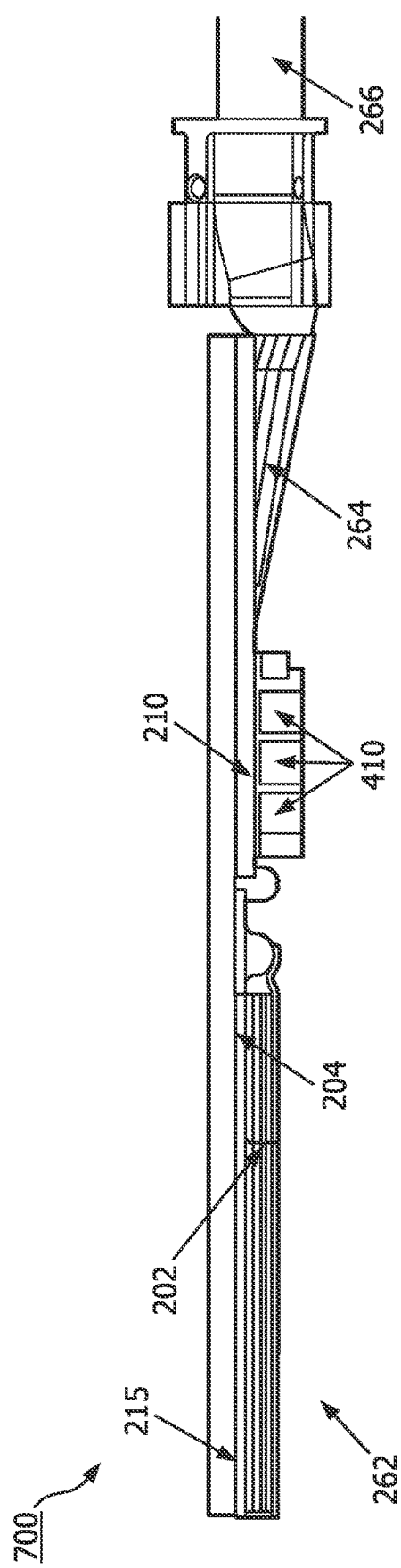
FIG. 7A is a right side view of the imaging assembly of the imaging device, according to aspects of the present disclosure.

FIG. 7A is a right side view 700 of the imaging assembly of the imaging device, according to aspects of the present disclosure. The right side view 700 includes the imaging core 262 adjacent to the interconnect board 210. Also shown are the electrical interconnections 264 and electrical cable 266. The right side view 700 further includes electronic components 410 mounted on the interconnect board 210. Also, the right side view 700 may include a backing layer 215.

Figure 7B:
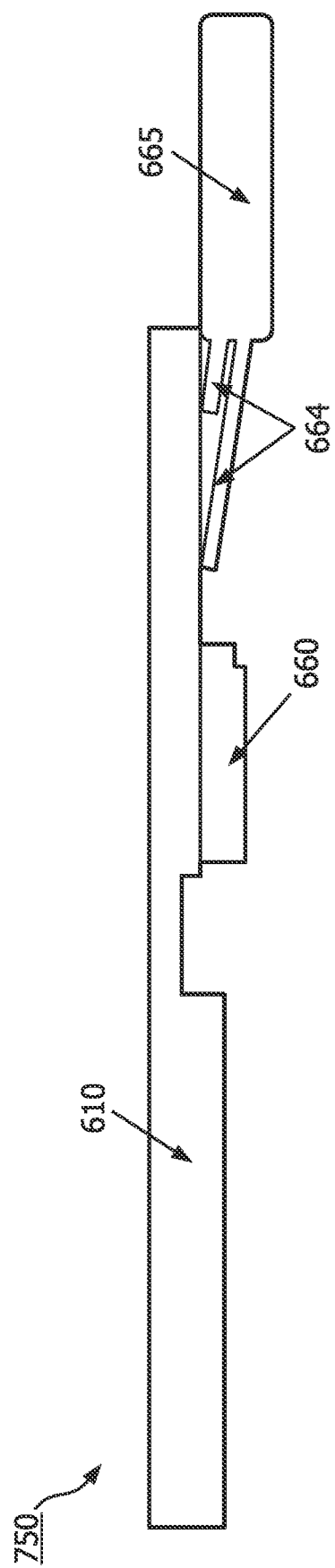
FIG. 7B is a graphical representation of a radiographic image of the right side view of the imaging assembly of FIG. 7A, according to aspects of the present disclosure.

FIG. 7B is a right side view 750 of a simulated radiographic image of the imaging assembly of an imaging device, according to aspects of the present disclosure. In some examples, the view 750 is a simulated silhouette, e.g., radiographic image of the imaging assembly 102. In some examples, the view 750 shows the layer 610 that includes the silhouette side image of the backing layer 215 and the layers on top of the backing layer. In some examples, the view 750 also shows the silhouette images 660, 665, and 664 as described before. Because of the non-symmetric arrangement of the electronic components 410, the left side view of FIG. 6B is distinguishable from the bottom view of FIG. 7B.

In some embodiments, a radiographic imaging unit with the X-ray source 142 on the top and the X-ray detector 144 on the bottom is used for obtaining the images 650 and 750 of FIGS. 6B and 7B such that the X-rays travel from top to bottom in a way that they impinge from the top to the body and emerge from the bottom of the body. In some embodiments, as shown in FIGS. 6A and 7A, the electronic components 410 have an asymmetric configuration with respect to the thickness of the imaging assembly 102 as viewed from a side. As the result of this asymmetry, the silhouette images 460 of FIGS. 6B and 7B are not symmetrical with respect to the top-down of the image 650 and 750. Thus, in some examples, when a radiographic image similar to the image 650 shown in FIG. 6B is obtained, based on the configuration of the silhouette images 460, as compared to the electronic components 410 of FIG. 6A, it may be concluded that the imaging assembly 102 is focusing to the right. In some examples, when a radiographic image similar to the image 750 shown in FIG. 7B is obtained, based on the configuration of the silhouette images 460 as compared to the electronic components 410 of FIG. 7A, it may be concluded that the imaging assembly 102 is focusing to the left. In some embodiments, the control and processing system 103 may distinguish between the configuration of the silhouette images 460 in FIGS. 6B and 7B and recognize if the imaging assembly is focusing to the right or left.

FIG. 8A is a diagram 800 showing a body organ and an imaging device inside the body organ, according to aspects of the present disclosure. In some examples, the body organ is a human heart 810 and as shown a catheter 820 which is consistent with the imaging device 110 of FIG. 1 is inserted into the human heart 810. As shown in diagram 800, the imaging assembly 830 of the catheter 820 that is consistent with the imaging assembly 102 of FIG. 1 is sending the ultrasonic energy upward.

FIG. 8B is a diagram 850 showing the body organ and the imaging device inside the body organ, according to aspects of the present disclosure. As shown in diagram 850, the imaging assembly 860 of the catheter 820 that is consistent with the imaging assembly 102 of FIG. 1 is sending the imaging waves downward. Therefore, the imaging assembly of FIGS. 8A and 8B may generate images of two different location of the heart and thus the viewer of the generated images may need to know the orientation of the imaging assembly inside heart for at least analyzing the image and deciding which direction to send the catheter. In some examples, as shown in FIGS. 8A and 8B, the imaging assemblies 830 and 860 are focusing in opposite directions. Because of the asymmetry of the electronic components, the radiographic images of the imaging assemblies in FIGS. 8A and 8B make look similar to the images 650 and 750 of FIGS. 6B and 7B. Therefore a human viewer or the control and processing system 130 may recognize the direction that the imaging assembly is focusing at.

As shown in FIGS. 2, 6A, and 7A, the imaging assembly 102 can also include an integrated circuit 204 and another electronic component, e.g., an interconnect board 210, in electrical communication with the imaging elements 202, each other, and/or the electrical cable 266. In some embodiments, the integrated circuit 204 and the interconnect board 210 can be rigid or flexible printed circuit assemblies. For example, the integrated circuit 204 is an application specific integrated circuit (ASIC), configured to control operation of the imaging elements 202. For example, the integrated circuit 204 can drive the transducer elements 202, provide switching between signal lines, generation of the excitation pulse, and/or other features associated with intraluminal imaging, imaging fluid filled structures, or imaging within a body of a patient. In some examples, the integrated circuit 204 may be a micro-beamformer integrated circuit (IC) that can control the array of imaging elements 202 and can perform beam forming for the array imaging elements 202. In some embodiments, the transducer elements 202 are formed, on a substrate of the integrated circuit 204. In some embodiments, the array of ultrasound imaging transducers 202 are directly flip-chip mounted to the integrated circuit 204. Piezoelectric elements 202 typically would be attached to the IC by flip-chip mounting an assembly of acoustic layers and sawing into individual elements. MUT elements may be flip-chip mounted as a unit or grown directly on top of the integrated circuit 204. In some examples, mass termination of the acoustic imaging elements 202 is done at the integrated circuit 204. In some embodiments, the integrated circuit 204 lies directly underneath the array of acoustic elements 202 and is electrically connected to them. The integrated circuit 204 may be in physical and thermal contact with the imaging elements 202.

Figure 9:
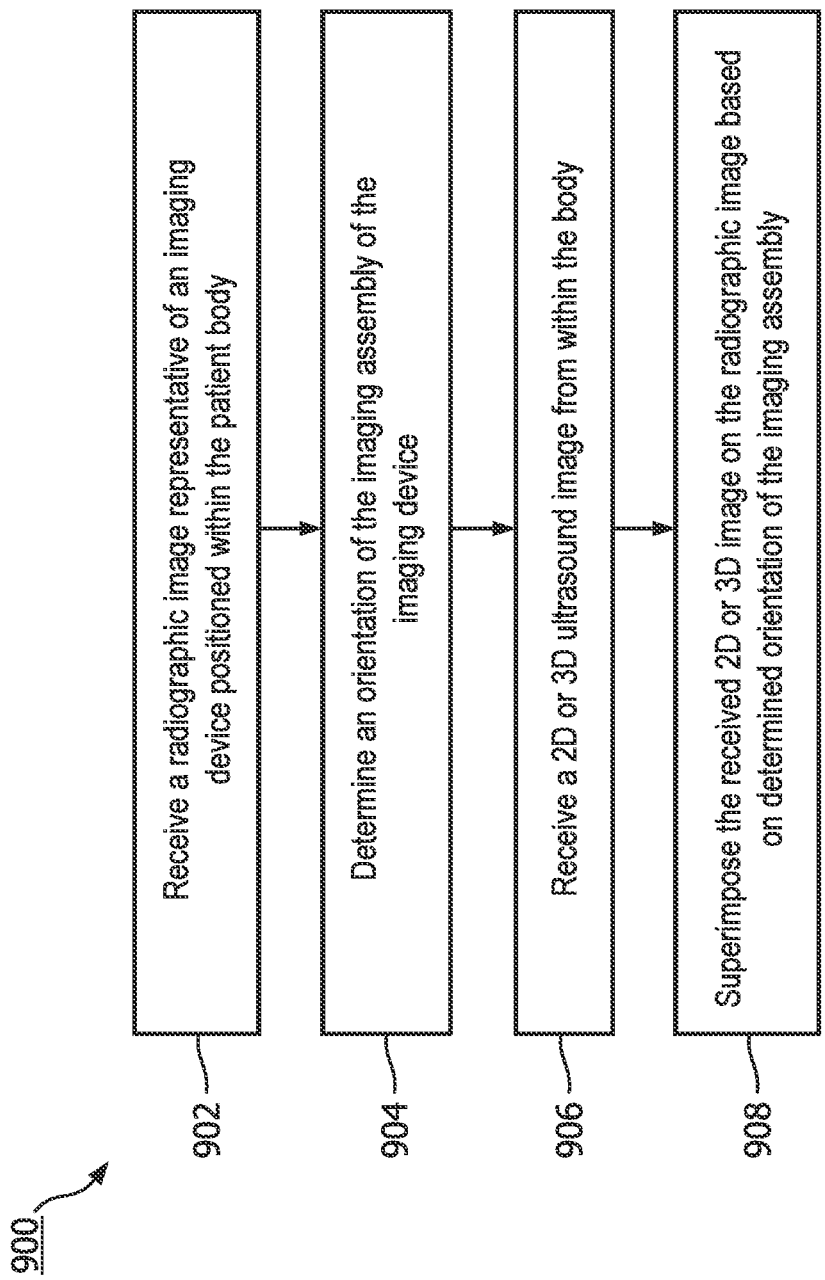
FIG. 9 is a flow diagram of a method of imaging within a patient body, according to aspects of the disclosure.

FIG. 9 provides a flow diagram illustrating a method 900 imaging within a patient. It is understood that the steps of method 900 may be performed in a different order than shown in FIG. 9, additional steps can be provided before, during, and after the steps, and/or some of the steps described can be replaced or eliminated in other embodiments. The steps of the method 900 can be carried out by a user/operator of an imaging device.

At step 902, the method 900 includes receiving a radiographic image representative of an imaging device positioned within the patient body. In some embodiments and as shown in FIG. 1 the radiographic image is received at a computing device, e.g., the control and processing system 130, in communication with a radiographic imaging unit. In some examples and as shown in FIG. 1, the radiographic imaging unit includes an X-ray source 142 and the X-ray detector 144. In some examples and as shown with respect to FIG. 8, a catheter including an imaging assembly 102 is inserted in the body. In some examples and as shown with respect to FIG. 3, the radiographic image includes the image of the body and the image 310 of the catheter which is consistent with the imaging device 110 of FIG. 1.

At step 904, the method 900 includes determining an orientation of the imaging assembly of the imaging device. In some examples, the orientation of the imaging assembly 102 is determined using the radiopaque pattern of the plurality of electronic components in the radiographic image. The plurality of electronic components are show with respect to FIGS. 4A, 5A, 6A, and 7A and the radiographic image of the plurality of electronic components are shown with respect to FIGS. 4B, 5B, 6B, and 7B. In some examples, the plurality of electronic components is arranged such that from the radiographic image of the plurality of electronic components the orientation of the imaging assembly 102 with respect to the body can be determined. In some examples, a single electronic component may be designed such that based on the radiographic image of that electronic component alone the orientation of the imaging assembly 102 with respect to the body can be determined.

At step 906, the method 900 includes receiving a 2D or 3D ultrasound image from within the body. For example, the 2D or 3D ultrasound image may be an image of a portion of the heart. In some examples the 2D or 3D image is received by the control and processing system 130 from the imaging device 110. In some examples, the received 2D or 3D image is an ultrasonic image.

At step 908, the method 900 includes superimposing the received 2D or 3D image on the radiographic image based on the determined orientation of the imaging assembly. In some examples, the received 2D or 3D image is superimposed by the control and processing system 130 on the radiographic image. In some examples, in the superimposed image, a direction of focus of the imaging assembly is indicated by, for example, displaying a shape of the imaging assembly, text message, etc.

In some embodiments, the electronic components may be structured in multiple asymmetric configurations such that the multiple configurations are recognizable in the radiographic image of the imaging assembly. In some examples, each of the multiple configurations may correspond to imaging assembly operating at a different frequency such that a first configuration of the electronic components may correspond to an ultrasound probe operation at 6 MHz and a second configuration of the electronic components may correspond to an ultrasound probe operation at 10 MHz. Thus, in some examples, the control and processing system 130 may analyze the obtained radiographic image and recognize the location, orientation, and the frequency of operation of the imaging assembly. In some examples, based on the frequency of operation of the probe, the control and processing system 130 can determine a field of view of the probe and then may limit the X-ray exposure of the body based on the determined field of view.

In some embodiments, the imaging device includes characteristic and discernible silhouettes in each of three orthogonal planes such that left can be discerned from right, top from bottom and back from front. In some examples, the size of the imaging device is such that variations in the profile of the imaging device are big enough to be within the resolving power of the fluoroscopic system.

The embodiment as described above pertains to ICE but could readily be translated to other invasive ultrasound imaging devices such as intravascular ultrasound devices and trans-oesophageal probes.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
   an ultrasound imaging device for imaging within a body of a patient, comprising:
      a flexible elongate member configured to be inserted into the body of the patient;
      an imaging assembly disposed at a distal portion of the flexible elongate member, the imaging assembly comprising:
         an array of imaging elements;
         a circuit board comprising a first surface and an opposite, second surface; and
         a plurality of electronic components mounted only on the first surface and electrically coupled to the circuit board to perform an electrical function associated with imaging within the body of the patient using the array of imaging elements; and
   a computing device,
   wherein each of the plurality of electronic components is radiopaque such that the plurality of electronic components itself comprises a radiopaque arrangement, wherein the radiopaque arrangement comprises a top, a bottom, a first side, and a second side, wherein the radiopaque arrangement comprises an asymmetric shape such that:

the first side of the radiopaque arrangement comprises a first non-planar outline of the plurality of electronic components and a planar outline of the second surface; and the second side of the radiopaque arrangement comprises a different, second non-planar outline of the plurality of electronic components and the planar outline of the second surface, wherein the computing device is configured to determine an orientation of the ultrasound imaging device using at least one of the first non-planar outline or the second non-planar outline in a radiographic image.

2. The system of claim 1, wherein the plurality of electronic components comprises capacitors.

3. The system of claim 1, wherein the circuit board is disposed adjacent to the array of imaging elements.

4. The system of claim 1, further comprising a radiographic imaging unit configured to obtain the radiographic image, wherein the radiographic image comprises the ultrasound imaging device within the body of the patient, wherein the computing device is in communication with the radiographic imaging unit.

5. The system of claim 1, wherein the ultrasound imaging device is an intra-cardiac echocardiography device.

6. The system of claim 1, wherein the orientation of the ultrasound imaging device comprises an orientation of the imaging assembly, wherein the computing device is further configured to co-register imaging data obtained by the ultrasound imaging device and the radiographic image based on the orientation of the imaging assembly.

7. The system of claim 6, wherein the computing device is configured to output the co-registered imaging data and the radiographic image to a display.

8. The system of claim 6, wherein the computing device is configured to superimpose the imaging data on a corresponding location in the radiographic image based on the co-registering.

9. The system of claim 1, wherein the array of imaging elements comprises an outward surface and an inward surface, and wherein the ultrasound imaging device further comprises an integrated circuit adjacent to the inward surface of the array of imaging elements.

10. The system of claim 9, wherein the integrated circuit comprises a first surface and a second surface opposite the first surface, wherein the first surface of the integrated circuit is coupled to the array of imaging elements.

11. The system of claim 10, wherein the imaging assembly further comprises an acoustic backing material comprising a first surface and a second surface opposite the first surface, wherein the second surface of the integrated circuit is coupled to the first surface of the acoustic backing material.

12. The system of claim 9, wherein the circuit board comprises an interconnect board in communication with at least one of the array of imaging elements or the integrated circuit.

13. The system of claim 12, wherein the interconnect board is in contact with an acoustic backing material of the imaging assembly.

14. The system of claim 9, wherein the integrated circuit is configured to control the array of imaging elements.

15. A method of imaging within a patient body, comprising:

receiving, at a computing device in communication with a radiographic imaging unit, a radiographic image representative of an ultrasound imaging device positioned within the patient body, wherein the ultrasound imaging device comprises an imaging assembly disposed at a distal portion of a flexible elongate member, wherein the imaging assembly comprises:

an array of imaging elements;

a circuit board comprising a first surface and an opposite, second surface; and a plurality of electronic components mounted only on the first surface and electrically coupled to the circuit board to perform an electrical function associated with the array of imaging elements, wherein each of the plurality of electronic components is radiopaque such that the plurality of electronic components itself comprises a radiopaque arrangement, wherein the radiopaque arrangement comprises a top, a bottom, a first side, and a second side, wherein the radiopaque arrangement comprises an asymmetric shape such that:

the first side of the radiopaque arrangement comprises a first non-planar outline of the plurality of electronic components and a planar outline of the second surface; and the second side of the radiopaque arrangement comprises a different, second non-planar outline of the plurality of electronic components and the planar outline of the second surface; and determining, by the computing device, an orientation of the ultrasound imaging device using at least one of the first non-planar outline or the second non-planar outline in the radiographic image.

16. The method of claim 15, further comprising:

superimposing an image of the patient body obtained the ultrasound imaging device on the received radiographic image based on the determined orientation of the ultrasound imaging device.

* * * * *